United States Patent [19]

Hefner, Jr.

[11] Patent Number: 4,540,745

[45] Date of Patent: Sep. 10, 1985

[54] ALLYL STYRYL PYRIDINES AND PYRAZINES AND POLYMERS THEREOF

[75] Inventor: Robert E. Hefner, Jr., Lake Jackson, Tex.

[73] Assignee: The Dow Chemical Company, Midland, Mich.

[21] Appl. No.: 632,342

[22] Filed: Jul. 19, 1984

[51] Int. Cl.$^3$ ............................................ C08F 283/06
[52] U.S. Cl. ...................................... 525/401; 528/246
[58] Field of Search ......................... 525/401; 528/246

[56] References Cited

U.S. PATENT DOCUMENTS

| | | | |
|---|---|---|---|
| 4,362,860 | 12/1982 | Ratto et al. | 528/246 X |
| 4,471,107 | 9/1984 | Peake | 528/246 X |
| 4,500,690 | 2/1985 | Latulip | 525/502 |

*Primary Examiner*—Lucille M. Phynes

*Attorney, Agent, or Firm*—B. G. Colley

[57] ABSTRACT

Allyl ether capped styryl pyridines and styryl pyrazines are prepared by allylating with an allylating agent such as allyl halide or allyl methyl carbonate the reaction product of (A) a substituted pyridine and/or pyrazine with (B) a substituted aromatic aldehyde with the proviso that at least one of the components (A) or (B) contains a hydroxyl group which is susceptible to allylation. These allylated styryl pyridines and pyrazines can be homopolymerized or copolymerized with other materials to produce polymers having excellent high temperature resistance, good mechanical strength and excellent processability and are used to make cured composites with heat resistant fibers that have applications in high temperature environments such as engine compartments and/or fire walls.

10 Claims, No Drawings

ALLYL STYRYL PYRIDINES AND PYRAZINES AND POLYMERS THEREOF

BACKGROUND OF THE INVENTION

This invention relates to thermosettable allyl styryl pyridine and pyrazine compositions having improved processability and excellent thermal stability.

Hydroxystyryl pyridines are known from Yan et al, Org. Coatings and Applied Science Proceedings, 46:482-488 (ACS Preprint 183 National Meeting, Las Vegas, Nevada 1982); Chiang et al, J. Org. Chem., 10:21-25 (1945); Bramsch, Chem. Berichte, 42:1193-1197 (1909); Franke, Chem. Berichte, 38:3724-3728 (1905) and Ser. No. 588,597 filed Mar. 12, 1984 now U.S. Pat. No. 4,515,938 granted, May 7, 1985. The hydroxystyryl pyridines typically possess high melting points and low solvent solubility, hence conventional processing, such as impregnation of a fiberglass mat by hot melt or solvent impregnation techniques is extremely difficult. Hydroxyl groups present in the cured (thermoset) hydroxystyryl pyridines can induce moisture sensitivity and susceptibility to chemical attack by solvents as well as aqueous media such as dilute sodium hydroxide solution. Reactivity of the hydroxystyryl pyridines is poor, with prolonged cure temperatures of 250° C. to 300° C. or higher being required. The condensation curing reaction to provide a hydroxypolystyryl pyridine evolves water, hence voids and bubbles are typically present in the cured products. These defects are deleterious to the mechanical properties of the cured product.

More recently, vinyl styryl pyridines and vinyl polystyryl pyridines have been developed, for example as taught by Ratto, et al in U.S. Pat. No. 4,362,860. Said vinyl styryl pyridine compositions provide some improvement in reactivity, being initially cured at temperatures of 150° C. to 200° C., however, many of the aforementioned problems remain. The reaction times and reaction temperatures required for synthesis of vinyl styryl pyridines frequently dimish the polymerizable vinyl group content of the finished product thus leading to only an incremental improvement in reactivity.

Various other styryl pyridine compositions are known, however, these compositions typically possess the aforementioned problems.

The present invention provides novel thermosettable allyl styryl pyridine and/or pyrazine compositions having excellent processability being typically low melting, highly solvent soluble and highly reactive. Curing does not evolve gaseous products, such as water vapor, thus void-free cured products are readily obtained. All of these property improvements are obtained without a significant loss in thermal stability. The process of the present invention uses a transcarbonation reaction wherein allyl methyl carbonate stoichiometrically reacted with the hydroxystyryl pyridine and/or pyrazine provides essentially total allylation of the hydroxyl groups of the hydroxystyryl pyridine (pyrazine). Alternately, a direct allylation reaction is employed wherein an allyl halide is stoichiometrically reacted with the hydroxyl groups of the hydroxy styryl pyridine (pyrazine). These compositions are useful in the preparation of homopolymers or copolymers which can take form of unfilled or filled castings, fiberglass laminates, graphite or carbon fiber reinforced composites, coatings and the like.

SUMMARY OF THE INVENTION

One aspect of the present invention concerns allyl styryl pyridine or allyl styryl pyrazine compositions resulting from allylating a product resulting from reacting (A) at least one of
  (1) one or more pyridine compounds represented by the formula

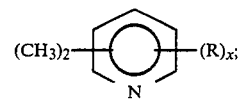

I.

(2) one or more pyrazine compounds represented by the formula

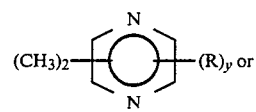

II.

(3) a mixture of (1) and (2); with
(B) a substituted aromatic aldehyde represented by the formula

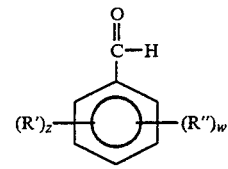

III.

wherein each R is independently hydrogen, hydroxyl, methyl or ethyl; each R' is independently a hydroxyl or

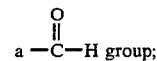

a $-\overset{\text{O}}{\underset{\|}{C}}-H$ group;

each R" is independently hydrogen, methyl or ethyl; x has a value of 3; y has a value of 2; z has a value of 1 or 2; w has a value of 3 or 4; the sum of z and w has a value of 5; and with the proviso that at least one of R or R' is a hydroxyl group to provide a hydroxyl functional precursor which is then reacted with (C) an allylating agent whereby at least about one percent of the rings of the reaction product of (A) and (B) possess allyl groups.

Allylation of the resultant hydroxy styryl pyridine and/or pyrazine (HSP) precursor is accomplished via a transcarbonation reaction using allyl methyl carbonate or a direct allylation reaction using allyl halide and an alkaline agent.

Allyl methyl carbonate is usually prepared from the reaction of allyl alcohol and dimethyl carbonate to give a mixture of allyl methyl carbonate and diallyl carbonate. Both the crude mixture and the pure allyl methyl carbonate can be used herein as the allylating agent as well as allyl halides such as allyl chloride, allyl bromide."

Another aspect of the present invention pertains to homopolymers of the aforementioned allyl styryl pyridines and/or pyrazines.

A further aspect of the present invention pertains to copolymerizable mixtures of
(A) at least one of the aforementioned allyl styryl pyridines and/or allyl styryl pyrazines; and
(B) at least one material selected from
  (1) styryl pyridines and/or prepolymers and polymers thereof;
  (2) vinyl styryl pyridines and/or prepolymers and polymers thereof;
  (3) bismaleimides and/or polymaleimides;
  (4) alkenylphenol capped styryl pyridines and/or prepolymers and polymers thereof;
  (5) hydroxystyryl pyridines and/or prepolymers and polymers thereof;
  (6) allyl monomers and/or prepolymers thereof; or
  (7) mixtures thereof in any proportion and combination.

Another aspect of the present invention pertains to polymers and/or cured products of the aforementioned copolymerizable and/or curable mixtures.

A further aspect of the present invention pertains to articles prepared from the aforementioned polymers and/or cured products.

DETAILED DESCRIPTION OF THE INVENTION

The allyl styryl pyridine and/or pyrazine compositions of the present invention are prepared using a hydroxy functional styryl pyridine and/or pyrazine (HSP) precursor. The HSP precursor may be monomeric, oligomeric (prepolymer), polymeric or a mixture thereof.

The HSP precursor is prepared by condensation reaction of (A) a substituted pyridine or mixture of substituted pyridines represented by formula I above and/or (B) a substituted pyrazine or mixture of substituted pyrazines represented by formula II above, with (C) a substituted aromatic aldehyde or mixture of substituted aromatic aldehydes represented by formula III above.

Suitable acidic catalysts which can be employed for the condensation reaction of a substituted pyridine (formula I) and/or a substituted pyrazine (formula II) and a substituted aromatic aldehyde (formula III) are sulfuric acid, hydrochloric acid, $ZnCl_2$, acetic anhydride, $AlCl_3$, toluenedisulfonic acid, trichloroacetic acid, acetic acid and the like. The catalysts are used in amounts from 0.5 to 20 weight percent based on the total weight of the reactants and preferably in amounts from 2 to 5 weight percent. It is to be understood that the reaction can proceed in the absence of catalyst but the reaction time is typically increased.

The condensation reaction of a substituted pyridine (formula I) and/or a substituted pyrazine (formula II) and a substituted aromatic aldehyde (formula III) is conducted at a temperature from about 130° to about 230° C., preferably 140° to 190° C. for a period of from about 0.5 to 24 hours, preferably 1 to 8 hours. The reaction is conducted in the absence of oxygen and suitably in a nitrogen atmosphere, preferably with removal of water generated by the reaction.

Examples of useful substituted pyridines (formula I) are 2,3-dimethylpyridine; 2,4-dimethylpyridine; 2,5-dimethylpyridine; 2,6-dimethylpyridine; 3,4-dimethylpyridine; 3,5-dimethylpyridine; 3,5-dimethyl-2-ethylpyridine; 2,3,4,6-tetramethylpyridine; 2,3,5-trimethylpyridine; 2,3,6-trimethylpyridine; 2,4,5-trimethylpyridine; 2,4,6-trimethylpyridine; 2,4-dimethyl-6-hydroxypyridine; 2,6-dimethyl-4-hydroxypyridine; 2,6-dimethyl-3-hydroxypyridine and 2,4,6-trimethyl-5-hydroxypyridine.

Examples of useful substituted pyrazines (formula II) are 2,5-dimethylpyrazine; 2,3-dimethylpyrazine; 2,5-dimethylpyrazine; 2,3,5-trimethylpyrazine; 2,3,5,6-tetramethylpyrazine; 2,5-dimethyl-6-hydroxypyrazine and 2,5-dimethyl-3-ethylpyrazine.

Examples of useful substituted aromatic aldehydes (formula III) are 2-hydroxybenzaldehyde, 3-hydroxybenzaldehyde, 4-hydroxybenzaldehyde, 2-hydroxy-3-methylbenzaldehyde, 2-hydroxy-3-ethylbenzaldehyde, 4-hydroxy-3,5-dimethylbenzaldehyde, terephthaldehyde, 2,6-dihydroxybenzaldehyde, methylterephthaldehydes, dimethylterephthaldehydes and ethylterephthaldehydes.

The condensation reaction can be conducted using a mole ratio of a substituted pyridine (formula I) and/or a substituted pyrazine (formula II) to substituted aromatic aldehyde (formula III) of from about 0.33:1 to about 6:1, preferably 1:1 to 3:1. It is to be understood that the foregoing reactants can be used in combination as in an initial mixture of each or by the sequential addition during the reaction to achieve beneficial results.

Preferred HSP precursors for use in the present invention are prepared by acid catalyzed condensation reaction of 2,4,6-trimethylpyridine and 4-hydroxybenzaldehyde; 2,4,6-trimethylpyridine, 2,6-dimethylpyridine and 4-hydroxybenzaldehyde; 2,4,6-trimethylpyridine, and 4-hydroxy-3,5-dimethylbenzaldehyde; 2,3,5,6-tetramethylpyrazine and 4-hydroxybenzaldehyde and the like.

Several types of HSP precursors are described by Chiang and Hartung in *Journal of Organic Chemistry*, Volume 10, pages 21–25 (1945); by Bramsch in *Chemische Berichte*, Volume 42, pages 1193–1197 (1909); Franke in *Chemische Berichte*, Volume 38, pages 3724–3728 (1905) and Yan, et al in *Organic Coatings and Applied Polymer Science Proceedings*, Volume 46, pages 482–488 (1982) published by American Chemical Society.

A monomeric HSP precursor can be oligomerized (prepolymerized) typically by maintaining at a temperature of from about 180° to 300° C. for from about 0.5 to 8 hours. Polymerization is completed at a temperature of from about 250° to 300° C. for from about an additional 1 to 10 hours. The HSP product obtained from the aforementioned condensation reaction can be fractionated to provide monomeric and oligomeric HSP precursors using methods well known to the skilled artisan. Such methods include, for example, preparative gel permeation chromatography, solvent fractionation or extraction and recrystallization.

Preparation of a specific HSP precursor is summarized, as follows:

PREPARATION 1—Hydroxy Functional Styryl Pyridine (HSP) Prepared Using 2,4,6-Trimethylpyridine; 2,6-Dimethylpyridine and 4-Hydroxybenzaldehyde Trimethylpyridine (588.0 grams, 4.85 moles) and zinc chloride catalyst (26.0 grams) were added to a reactor and heated with stirring under a nitrogen atmosphere to a reflux. The reaction mixture was cooled to 150° C. then p-hydroxybenzaldehyde (887.0 grams, 7.26 moles) was added in 100 to 150 gram aliquots over a 110 minute period and so as to maintain the reaction temperature between 145° to 154° C. After addition of the p-hydroxybenzaldehyde was complete, the reaction temperature was increased to 160° C. After 4 hours of reaction at the 160° C. temperature, 2,6-dimethylpyridine (560.0 grams, 5.23 moles) was added to the reactor, then collection of a methylpyridines—water azeotrope into a Dean Stark trap—cold water condensor assembly began. After 150 milliliters of azeotrope was collected, 150 milliliters of fresh 2,6-dimethylpyridine was added to the reaction mixture. The reaction was allowed to progress for an additional 4 hours at the 160° C. reaction temperature followed by cooling to room temperature. After this time, the final reaction stoichiometry was a 1 to 1.5 to 1 mole ratio of 2,4,6-trimethylpyridine to p-hydroxybenzaldehyde to 2,6-dimethylpyridine.

Portions of the hydroxystyryl pyridine product were worked up as needed by vigorously mixing the dark caramel colored viscous reaction product from above with an excess of methylene chloride. This provided a methylene chloride insoluble light orange colored powder which was recovered by filtration. The powder was multiply washed with an excess of boiling water and then dried under vacuum at 100° C. to a constant weight. Infrared spectrophotometric analysis demonstrated a lack of aldehyde absorbance (1670 cm$^{-1}$), thus indicating that the hydroxybenzaldehyde was totally reacted. As expected, trans-unsaturation absorbance was found to be present (970 cm$^{-1}$). Aromatic carbon-oxygen absorbance (1250 cm$^{-1}$) confirmed the presence of the phenolic groups. Titration demonstrated the presence of 8.04 percent by weight phenolic hydroxyl groups. The product had a melting point range of 160° to 170° C.

Allylation of the HSP precursor to provide the allyl styryl pyridine (pyrazine) compositions of the present invention is preferably accomplished using the transcarbonation reaction wherein allyl methyl carbonate or a crude mixture containing allyl methyl carbonate is reacted with the HSP precursor in the presence of a catalytic amount of palladium on carbon and triphenylphosphine. Reaction of a 1 to 1 mole ratio of allylmethyl carbonate with the hydroxyl groups of the HSP precursor provides an allyl ether capped hydroxystyryl pyridine (pyrazine) wherein substantially all of the hydroxyl (—OH) groups of the HSP precursor are converted to —O—CH$_2$—CH=CH$_2$ groups.

Although less preferred, allylation of the HSP precursor to provide the allyl styryl pyridine (pyrazine) compositions may be accomplished by direct allylation reaction of the HSP precursor with an allyl halide such as allyl chloride in the presence of an alkaline agent such as an aqueous solution of alkali metal hydroxide. If desired, inert solvents such as 1,4-dioxane and phase transfer catalysts such as benzyltrialkylammonium halides or tetraalkylammonium halides can be employed. Reaction temperatures of from about 25° to about 150° C. are operable with temperatures of 50° to 100° C. being preferred. Reaction times of from about 15 minutes to about 8 hours are operable with reaction times of from about 2 hours to 6 hours being preferred. Reaction of a 1 to 1 mole ratio of allyl halide with the hydroxyl groups of the HSP precursor provides an allylated hydroxystyryl pyridine (pyrazine) wherein the major amount (80 or more percent) of the hydroxyl (—OH) groups of the HSP precursor are converted to —O—CH$_2$—CH=CH$_2$ groups. A minor amount (20 percent or less) of the allyl groups have undergone thermally induced Claisen rearrangement and are thus present on the aromatic ring ortho and/or para to the hydroxyl —OH groups from which the rearrangement occurred.

The reaction of less than a 1 to 1 mole ratio of allyl methyl carbonate in the transcarbonation reaction or allyl halide in the direct allylation reaction with the hydroxyl groups of the HSP precursor provides partial allylation of the HSP precursor with some free hydroxyl groups remaining. Although these partially allylated styryl pyridine (pyrazine) compositions are less preferred, they are still useful compositions of the present invention.

The reaction of the allyl methyl carbonate in the transcarbonation reaction or allyl halide in the direct allylation reaction with the hydroxyl groups of the HSP precursor is conveniently followed by infrared spectrophotometric analysis and/or nuclear magnetic resonance spectroscopy.

The homopolymers (or copolymers) of the allyl styryl pyridines and/or pyrazines are prepared by heating with or without a free-radical forming catalyst and/or accelerator. Temperatures of from about 120° to about 350° C. are typically employed in the homopolymerization (curing) with temperatures of about 150° to about 250° C. being preferred. Suitable free radical forming catalysts which may optionally be used herein include the organic peroxides and hydroperoxides and azo or diazo compounds at concentrations of 0.001 to 2 percent by weight. Suitable accelerators which may optionally be used herein include the metal salts of an organic acid at concentrations of 0.001 to 0.5 percent by weight. Preferred free radical forming catalysts include t-butyl peroxybenzoate, dicumyl peroxide, di-t-butylperoxide, mixtures thereof and the like. Preferred accelerators include cobalt naphthanate and cobalt octoate. Partial homopolymerization (oligomerization or prepolymerization or B-staging) of the compositions of the present invention may be affected by using lower homopolymerization temperatures and/or shorter homopolymerization reaction times. Curing of the prepolymerized resin may then be completed at a later time or immediately following prepolymerization to comprise a single curing step. The progress of the homopolymerization can conveniently be followed by viscometry and/or infra-red spectrophotometric analysis.

The copolymers of the allyl styryl pyridines and/or pyrazines are prepared by heating of a mixture of the aforementioned composition with one or more of the following:

(A) styryl pyridines and/or prepolymers and polymers thereof;
(B) vinyl styryl pyridines and/or prepolymers and polymers thereof;
(C) bismaleimides and/or polymaleimides;
(D) alkenylphenol capped styryl pyridines and/or prepolymers and polymers thereof;
(E) hydroxystyryl pyridines and/or prepolymers and polymers thereof;
(F) allyl monomers and/or prepolymers;
(G) mixtures thereof.

Copolymerizable mixtures of the allyl styryl pyridines and/or pyrazines with (A) through (G) above can be formed and copolymerized in all proportions. Previously described conditions suitable for preparation of the homopolymers of this invention may also be used to prepared the copolymers of this invention.

The bis or polymaleimides optionally employed herein are represented by formulas

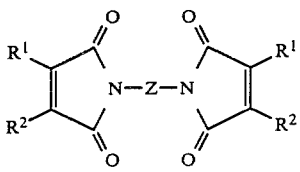 (IV)

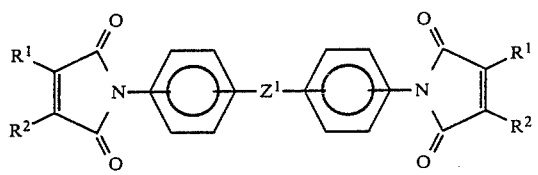 (V)

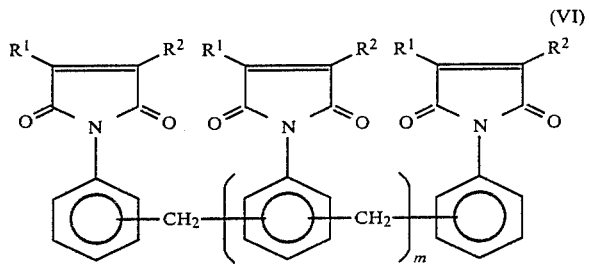 (VI)

wherein each $R^1$ and $R^2$ are independently hydrogen or a hydrocarbyl group having from 1 to 3 carbon atoms; Z is a divalent hydrocarbyl group having from 2 to about 12 carbon atoms; $Z^1$ is a direct bond, a divalent hydrocarbyl group with 1 to about 5 carbon atoms, —S—, —S—S—, —O—,

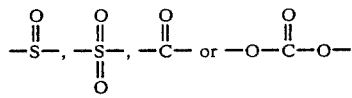

and m has an average value of 0.01 to about 10.

Typical bis or polymaleimides represented by formulas IV, V and VI include N,N'-ethylenebismaleimide, N,N'-ethylenebis(2-methylmaleimide), N,N'-hexamethylenebismaleimide, N,N'-(oxydi-p-phenylene)bismaleimide, N,N'-(methylenedi-p-phenylene)bismaleimide, N,N'-(methylenedi-p-phenylene)bis(2-methylmaleimide), N,N'-(thiodi-p-phenylene)bismaleimide, N,N'-(sulfonyldi-m-phenylene)bismaleimide, N,N'-(isopropylidenedi-p-phenylene)bismaleimide, polymethylene polyphenylene polymaleimides and the like. The bis or polymaleimides may be used either alone or in any combination. The bis or polymaleimides can be prepared by reacting per amine group a stoichiometric quantity of a maleic anhydride with a diamine or polyamine in the presence of a suitable solvent. Methods for the preparation of the bis and polymaleimides are taught by U.S. Pat. Nos. 2,444,536 and 2,462,835.

The styrylpyridines and/or prepolymers and polymers thereof optionally employed herein are described by Ropars, et al in U.S. Pat. No. 3,994,862 and by Malassine et al in U.S. Pat. No. 4,163,740 which are incorporated herein by reference.

The vinylstyrylpyridines and/or prepolymers and polymers thereof optionally employed herein are described by Hsu, et.al. in Vinylstyrylpyridine-Modified Bismaleimide Composite Resins presented to the 29th National SAMPE Symposium, April 3–5, 1984 and published on pages 1034–1042 of the proceedings of that symposium, as well as by Ratto, et al in U.S. Pat. No. 4,362,860.

The alkenylphenol capped styrylpyridines and/or prepolymers and polymers thereof optionally employed herein are described in Ser. No. 609,156 filed May 11, 1984 now U.S. Pat. No. 4,500,690, granted Feb. 19, 1985.

The hydroxy styryl pyridines and/or prepolymers and polymers thereof optionally employed herein are prepared based on the references previously cited herein.

The allyl monomers and/or prepolymers optionally employed herein are selected from the group consisting of the allyl-s-triazines, allyl ethers, allyl esters, diethylene glycol bis(allylcarbonate)s and phosphorus containing allyl monomers and/or prepolymers. Said allyl monomers and/or prepolymers are thoroughly described in the Encyclopedia of Polymer Science and Technology, Volume 1, pages 750 to 807 (1964) published by John Wiley and Sons, Inc. which is incorporated herein by reference.

Preferred allyl monomers and/or prepolymers thereof include triallyl isocyanurate, 2,4,6-tris(allyloxy)-s-triazine, hexaallylmelamine, hexa(allyoxymethyl)-melamine, trimethylolpropane diallyl ether, 1,2,3-methallyloxypropane, hexamethallyldipentaerythritol, diallyl phthalate, diallyl isophthalate, diethylene glycol bis(allylcarbonate) and allyl diphenyl phosphate. The allyl monomers and/or prepolymers may be used alone or in any combination.

The allyl styryl pyridine and/or pyrazine copolymers can be prepared in a similar manner to the preparation of homopolymers of allyl styryl pyridines and/or pyrazines.

The compositions of the present invention are useful in the preparation of homopolymers and copolymers with a high degree of thermal stability, moisture resistance and chemical resistance. Many of the copolymer compositions of the present invention also offer improved mechanical properties. The allyl styryl pyridine and/or pyrazine compositions offer excellent processability, solvent solubility and high reactivity and are thus suited to the preparation of a wide range of castings, preimpregnated cloths or mats, laminates with heat resistant fibers. Examples of these are graphite reinforced composites, carbon fiber reinforced composites, aramid fiber reinforced composites, asbestos fiber reinforced composites, glass fiber reinforced composites, metal fiber reinforced composites, coatings, highly filled castings, and the like. If desired, other materials can be employed, such as, for example, fillers, pigments, dyes, other additives and the like. These products are especially suited for use in high temperature environments such as engine compartments, fire-walls and the like.

The following examples are illustrative of the invention but are not to be construed as to limiting the scope thereof in any manner.

EXAMPLE 1

Synthesis of the Allyl Ether of a Hydroxy Styryl Pyridine

Allyl alcohol (101.58 grams, 1.75 moles), dimethyl carbonate (157.55 grams, 1.75 moles) and sodium methoxide catalyst (0.18 gram, 0.065 percent by weight)

were added to a reactor and maintained at room temperature (25° C.) with stirring under a nitrogen atmosphere. An equilibrium mixture of allylmethyl carbonate, diallyl carbonate and methanol was rapidly formed. After ten minutes a hydroxy functional styryl pyridine (16.9 grams, 0.1606 mole of hydroxy groups), triphenylphosphine (0.56 gram, 0.204 percent by weight) and 5% palladium on carbon (0.38 gram, 0.127 percent by weight) were added to the reactor and heating was started. The hydroxy functional styryl pyridine used herein was obtained from a reaction of 2,4,6-trimethylpyridine, 2,6-dimethylpyridine and p-hydroxybenzaldehyde as set forth in the foregoing Preparation 1. The reaction mixture was maintained for five hours at 80° C. and then filtered hot through Celite. The recovered filtrate was rotary evaporated at 100° C. and 10 mm Hg pressure for 30 minutes to provide a transparent, light amber colored oil (20.75 grams) which became a tacky solid at room temperature (25° C.).

Infrared spectrophotometric analysis of a film sample of the product confirmed the product structure for the allyl ether of the hydroxy functional styryl pyridine (aromatic carbon-oxygen absorbance (1250 cm$^{-1}$) accompanied by total absence of phenolic hydroxyl group absorbance (3300 cm$^{-1}$), trans-unsaturation absorbance (970 cm$^{-1}$)).

EXAMPLE 2

Homopolymerization of the Allyl Ether of a Hydroxy Styryl Pyridine

A 0.50 gram portion of the allyl ether of a hydroxy styryl pyridine from Example 1 and 0.0001 gram of cobalt naphthenate (6 percent active) were combined and then used to cast a film on an aluminum plate. The film and plate were placed in a vented, forced-air, convection type oven and cured at 225° C. for 4.0 hours. After this time, the cured homopolymer was recovered as a dark amber transparent film.

EXAMPLE 3

Thermogravimetric Analysis (TGA) of the Homopolymer of the Allyl Ether of a Hydroxy Styryl Pyridine Thermogravimetric analysis (TGA) of a 8.61 milligram portion of the homopolymer film from Example 2 was performed. Weight loss was recorded as a function of temperature at a 10° C. per minute rate of increase in a stream of nitrogen flowing at 35 cubic centimeters per minute. The results are reported in Table I.

TABLE I

| Weight Loss, % | | | | | | |
|---|---|---|---|---|---|---|
| 100° C. | 300° C. | 350° C. | 400° C. | 500° C. | 700° C. | 950° C. |
| 0 | 2.0 | 5.2 | 12.0 | 50.0 | 58.6 | 59.9 |

EXAMPLE 4

Copolymerization of the Allyl Ether of a Hydroxy Styryl Pyridine and Triallyl-s-triazine-2,4,6(1H, 3H, 5H)-Trione A 0.90 gram portion of the allyl ether of a hydroxy styryl pyridine from Example 1, 0.10 gram of triallyl-s-triazine-2,4,6(1H, 3H, 5H)trione [triallylisocyanurate] and 0.0002 gram of cobalt naphthenate (6 percent active) were combined and then used to cast a film on an aluminum plate. The film and plate were placed in a vented, forced-air, convection-type oven and cured at 225° C. for 4.0 hours (14,400 s). After this time, the cured copolymer was recovered as a dark amber transparent film.

EXAMPLE 5

Thermogravimetric Analysis (TGA) of the Copolymer of the Allyl Ether of a Hydroxy Styryl Pyridine and Triallyl-s-triazine-2,4,6(1H, 3H, 5H)-Trione Thermogravimetric analysis (TGA) of a 9.44 milligram portion of the homopolymer film from Example 4 was performed. Weight loss was recorded as a function of temperature at a 10° C. per minute rate of increase in a stream of nitrogen flowing at 35 cubic centimeters per minute. The results are reported in Table II.

TABLE II

| Weight Loss, % | | | | | | |
|---|---|---|---|---|---|---|
| 100° C. | 300° C. | 350° C. | 400° C. | 500° C. | 700° C. | 950° C. |
| 0 | 5.5 | 8.6 | 13.8 | 49.4 | 57.0 | 59.1 |

EXAMPLE 6

Copolymerization of the Allyl Ether of a Hydroxy Styryl Pyridine and N,N'-(methylenedi-p-phenylene)bismaleimide A 0.90 gram portion of the allyl ether of a hydroxy styryl pyridine from Example 1, 0.10 gram of N,N'-(methylenedi-p-phenylene)bismaleimide and 0.0002 gram of cobalt naphthenate (6 percent active) were combined and then used to cast a film on an aluminum plate. The film and plate were placed in a vented, forced-air, convection-type oven and cured at 225° C. for 4.0 hours. After this time, the cured copolymer was recovered as a dark amber transparent film.

EXAMPLE 7

Thermogravimetric Analysis (TGA) of the Copolymer of the Allyl Ether of a Hydroxy Styryl Pyridine and N,N'-(methylenedi-p-phenylene)bismaleimide Thermogravimetric analysis (TGA) of a 6.39 milligram portion of the homopolymer film from Example 6 was performed. Weight loss was recorded as a function of temperature at a 10° C. per minute rate of increase in a stream of nitrogen flowing at 35 cubic centimeters per minute. The results are reported in Table III.

TABLE III

| Weight Loss, % | | | | | | |
|---|---|---|---|---|---|---|
| 100° C. | 300° C. | 350° C. | 400° C. | 500° C. | 700° C. | 950° C. |
| 0 | 0.9 | 3.8 | 11.3 | 40.5 | 49.6 | 51.8 |

EXAMPLE 8

Copolymerization of the Allyl Ether of a Hydroxy Styryl Pyridine and N,N'-(methylenedi-p-phenylene)bismaleimide A 0.80 gram portion of the allyl ether of a hydroxy styryl pyridine from Example 1, 0.20 gram of N,N'-(methylenedi-p-phenylene)bismaleimide and 0.0002 gram of cobalt naphthenate (6 percent active) were combined and then used to cast a film on an aluminum plate. The film and plate were placed in a vented, forced-air, convection-type oven and cured at 225° C. for 4.0 hours. After this time, the cured copolymer was recovered as a dark amber film.

EXAMPLE 9

Thermogravimetric Analysis (TGA) of the Copolymer of the Allyl Ether of a Hydroxy Styryl Pyridine and N,N'-(methylenedi-p-phenylene)bismaleimide Thermogravimetric analysis (TGA) of a 18.17 milligram portion of the homopolymer film from Example 7 was performed. Weight loss was recorded as a function of temperature at a 10° C. per minute rate of increase in a stream of nitrogen flowing at 35 cubic centimeters per minute. The results are reported in Table IV.

TABLE IV

| Weight Loss, % | | | | | | |
|---|---|---|---|---|---|---|
| 100° C. | 300° C. | 350° C. | 400° C. | 500° C. | 700° C. | 950° C. |
| 0 | 1.8 | 5.2 | 14.2 | 42.6 | 53.0 | 53.9 |

EXAMPLE 10

Preparation of a Cured Glass Laminate Using Allyl Ether of a Hydroxy Styryl Pyridine and N,N'-(methylenedi-p-phenylene)bismaleimide A 16.76 gram portion of the allyl ether of hydroxy styryl pyridine from Example 1, 16.76 grams of N,N'-(methylenedi-p-phenylene)bismaleimide and 150 grams of methylene chloride were combined to form a mixture. A set of five 6-inch by 12-inch woven fiber-glass cloth pieces were then equally impregnated with the mixture. The fiberglass cloth used was a commercial-grade product treated with a proprietary coupling agent (Burlington 76-28 electrical laminating cloth) and had an average weight of 0.14 gram per square inch. The set of impregnated cloths were allowed to dry for 15 minutes at room temperature followed by additional drying in a vented, forced-air, convection-type oven for 5 minutes at 100° C. Each cloth was cooled and found to be tack-free at room temperature and then cut to provide ten 6-inch by 6-inch pieces which were loaded into a stainless steel frame and placed between stainless steel plates which had been treated with a silicone mold release. The plates were loaded into a 225° C. hot press (Pasadena Hydraulics, Inc. Model P-215) and maintained for four hours at 5000 psig. After this time a 6-inch by 6-inch by 1/16-inch light amber colored, rigid laminate was recovered and cut to provide a set of six 1-inch by 2-inch by 1/16-inch flexural strength test pieces. The flexural strength test pieces were tested on an Instron machine with standard methods (ASTM D-790). The Instron machine was set at a 1 inch span, 0.02 inch per minute crosshead speed and a 0.5 inch per minute chart speed. The Barcol hardness value is on the 934-1 scale. The results are reported in Table V.

TABLE V

| | |
|---|---|
| Barcol Hardness | 49 |
| Flexural Strength (psi) | 38,521 |
| Flexural Modulus (psi) | 2,934,000 |

EXAMPLE 11

A. Synthesis of Allyl Ether of Hydroxy Styryl Pyridine

Allyl alcohol (50.79 grams, 0.875 mole), dimethyl carbonate (78.775 grams, 0.875 mole) and sodium methoxide catalyst (0.09 gram, 0.065 percent by weight) were added to a reactor and maintained at room temperature (25° C.) with stirring under a nitrogen atmosphere. An equilibrium mixture of allyl methyl carbonate, diallyl carbonate and methanol was rapidly formed. After 10 minutes, a portion of the hydroxy styryl pyridine (8.45 grams, 0.040 mole of hydroxy groups) from Preparation 1, triphenylphosphine (0.28 gram, 0.204 percent by weight) and 5% palladium on carbon (0.19 gram, 0.137 percent by weight) were added to the reactor and heating was started. The reaction mixture was maintained for 4 hours at 80° C. then filtered hot through Celite. The recovered filtrate was rotary evaporated at 125° C. and 10 mm for 30 minutes to provide a transparent amber colored liquid (9.61 grams) which became a tacky solid at room temperature.

B. Reactivity of the Allyl Ether of Hydroxy Styryl Pyridine

A portion (0.2 gram) of the hydroxy styryl pyridine precursor used in A above and a portion (0.2 gram) of the allyl ether of hydroxy styryl pyridine from A above were placed in an oven and maintained at 185° C. The allyl ether of hydroxy styryl pyridine gelled to a solid in less than 15 minutes. The hydroxy styryl pyridine did not gel, even after 2 hours and 45 minutes at the 185° C. temperature.

EXAMPLE 12

TGA of a Thermally Cured Homopolymer of Allyl Ether of Hydroxy Styryl Pyridine

A 0.50 gram portion of the allyl ether of hydroxy styryl pyridine from Example 11-A was cured at 240° C. for 4.0 hours. After this time, the cured homopolymer was recovered as a black colored, rigid solid. TGA of a 7.90 milligram portion of the homopolymer was performed as a function of temperature at a 10° C. per minute rate of increase in a stream of nitrogen flowing at 35 cubic centimeters per minute. The results are reported in Table VI.

TABLE VI

| Weight Loss (%) | | | | | | |
|---|---|---|---|---|---|---|
| 100° C. | 300° C. | 350° C. | 400° C. | 500° C. | 700° C. | 950° C. |
| 0 | 1.7 | 3.6 | 9.1 | 49.6 | 57.4 | 60.9 |

EXAMPLE 13

Copolymerization of Allyl Ether of Hydroxy Styryl Pyridine and a Vinylpolystyryl Pyridine A 0.475 gram portion of the allyl ether of hydroxy styryl pyridine from Example 11-A, a vinylpolystyryl pyridine (0.119 gram) and acetone (0.50 gram) were thoroughly mixed until a homogeneous paste was formed. After devotalization of most of the acetone solvent at room temperature (25° C.), the mixture was placed in a vented, forced-air, convection type oven and maintained at 100° C. for 15 minutes. Curing was completed at 240° C. for 4.0 hours. After this time, the cured copolymer was recovered as a black colored, rigid solid.

The portion of vinylpolystyryl pyridine used herein was prepared from a reaction of 2,4,6-trimethylpyridine, terephthaldehyde and 2-methyl-5-vinyl pyridine as follows:

Terephthaldehyde (6.03 grams, 4.5 moles), 2,4,6-trimethylpyridine (363 grams, 3.0 moles) and acetic acid (540 grams, 9.0 moles) were added to a 4 liter glass resin kettle equipped with a mechanical stirrer, thermometer, nitrogen inlet, and condenser. The combined reactants were maintained under a nitrogen atmosphere with stirring then 5 minutes later acetic anhydride (918 grams, 9.0 moles) was added. The reaction mixture was heated to 140° C. and allowed to reflux. After 7 hours of reaction at the 140° C. temperature, the reaction mixture was cooled to 100° C. and 2-methyl-5-vinyl pyridine (536 grams, 4.5 moles) was added. The reaction mixture was reheated to 120° C. and maintained for an additional 7 hours. At that time, the reaction product was cooled to 100° C. and neutralized with 10 percent aqueous sodium hydroxide. The aqueous layer was decanted and the resulting mustard colored product was multiply washed with deionized water. The washed product was dissolved to form a 10 percent by weight solution in tetrahydrofuran and this solution was filtered. The filtrate was poured over ice and allowed to stand for five minutes. The precipitated product was recovered by adding the product-ice slurry to a large excess of deionized water followed by filtering. The solid, powdery product was recovered in the filter and again water washed, followed by drying under vacuum (30 inches Hg) at 75° C. Gel permeation chromatographic analysis using polystyrene standards demonstrated an average molecular weight of 2500.

EXAMPLE 14

TGA of the Copolymer of Allyl Ether of Hydroxy Styryl Pyridine and a Vinylpolystyryl Pyridine TGA of a 8.86 milligram portion of the copolymer from Example 13 was performed using the method of Example 12. The results are reported in Table VII.

TABLE VII

| | | | Weight Loss (%) | | | |
|---|---|---|---|---|---|---|
| 100° C. | 300° C. | 350° C. | 400° C. | 500° C. | 700° C. | 950° C. |
| 0 | 0.1 | 1.7 | 4.8 | 38.0 | 48.8 | 50.5 |

EXAMPLE 15

Copolymerization of Allyl Ether of Hydroxy Styryl Pyridine and a p-Isopropenylphenol Capped Polystyryl Pyridine A 0.475 gram portion of the allyl ether of hydroxy styryl pyridine from Example 11-A, a p-isopropenylphenol capped polystyryl pyridine (0.119 gram) and acetone (0.50 gram) were thoroughly mixed until a homogeneous paste was formed. After devolatilization of most of the acetone solvent at room temperature (25° C.), the mixture was placed in a vented, forced-air, convection type oven and maintained at 100° C. for 15 minutes. Curing was completed at 240° C. for 4.0 hours. After this time, the cured copolymer was recovered as a black colored, rigid solid.

The portion of p-isopropenylphenol capped polystyryl pyridine used herein was prepared from a reaction of 2,4,6-trimethylpyridine, terephthaldehyde and p-isopropenylphenol as follows:

Terephthaldehyde (890 grams, 6.6 moles) and 2,4,6-trimethylpyridine (534 grams, 4.4 moles) were added to a 2-liter glass resin kettle equipped with a mechanical stirrer, thermometer, nitrogen inlet and Dean Stark trap—cold water condensor assembly. The reaction mixture was heated to 100° C. using three infrared heating lamps and an automatic temperature controller. Once the terephthaldehyde had melted, the stirring was activated and 20 milliliters of concentrated sulfuric acid was added to the reactor. The nitrogen purge was set at 12.5 cubic centimeters per minute and maintained throughout the synthesis. Five minutes after addition of the sulfuric acid catalyst, the reaction mixture was heated to 175° C. and maintained therein for 0.75 hour during which time water and 2,4,6-trimethylpyridine collected into the Dean Stark trap. The reaction mixture was cooled to 155° C. then p-isopropenylphenol (140 grams, 1.2 moles) was added dropwise as a 50 percent by weight solution in acetone at such a rate as to maintain the reaction temperature between 152°–158° C. After 1 hour (including addition time for the p-isopropenylphenol-acetone solution) of reaction at 152°–158° C., the reaction mixture was cooled to room temperature (25° C.) and recovered as a solid product which was ground to a fine powder.

Portions of the powder were worked up as needed by dissolving in tetrahydrofuran followed by precipitation in water and filtration. The powder recovered by filtration was dissolved in acetone followed by precipitation in water and filtration. The solid, powdery product recovered in the filter was dried under vacuum (30 inches Hg) at 75° C. The melting point range of the p-isopropenylphenol capped polystyryl pyridine was 90° to 100° C.

EXAMPLE 16

TGA of the Copolymer of Allyl Ether of Hydroxy Styryl Pyridine and a p-Isopropenylphenol Capped Polystyryl Pyridine TGA of a 9.88 milligram portion of the copolymer from Example 15 was performed using the method of Example 12. The results are reported in Table VIII.

TABLE VIII

| | | | Weight Loss (%) | | | |
|---|---|---|---|---|---|---|
| 100° C. | 300° C. | 350° C. | 400° C. | 500° C. | 700° C. | 950° C. |
| 0 | 0.7 | 1.8 | 5.3 | 41.2 | 51.2 | 52.9 |

I claim:
1. A thermosettable allylated product which comprises the resinous reaction product of
(A) at least one of
(1) one or more pyridine compounds represented by the formula

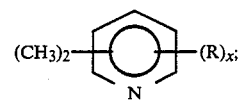

(2) one or more pyrazine compounds represented by the formula

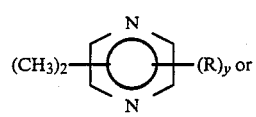

(3) a mixture of (1) and (2); with
(B) a substituted aromatic aldehyde represented by the formula III. 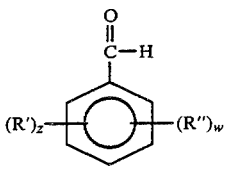

wherein each R is independently hydrogen, hydroxyl, methyl or ethyl; each R' is independently a hydroxyl or a

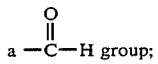

each R" is independently hydrogen, methyl or ethyl; x has a value of 3; y has a value of 2; z has a value of 1 or 2; w has a value of 3 or 4; the sum of z and w has a value of 5; and with the proviso that at least one of R or R' is a hydroxyl group to provide a hydroxyl functional precursor which is then reacted with (C) an allylating agent whereby at least about one percent of the rings of the reaction product of (A) and (B) possess allyl groups.

2. The reaction product of claim 1 wherein the molar ratio of (B) to (A) is in the range from about 0.33:1 to about 6:1 and the extent of allylation with said allylating agent is about 20 to 100 percent.

3. The reaction product of claim 1 wherein said allylating agent is selected from the group consisting of an allyl halide, allyl methyl carbonate, and a mixture of allyl methyl carbonate with diallyl carbonate.

4. Homopolymers of the reaction product of claim 1.

5. Copolymerizable mixtures of the reaction product of claim 1 with
   (A) styryl pyridines and/or prepolymers and polymers thereof;
   (B) vinyl styryl pyridines and/or prepolymers and polymers thereof;
   (C) bismaleimides and/or polymaleimides;
   (D) alkenylphenol capped styryl pyridines and/or prepolymers and polymers thereof;
   (E) hydroxystyryl pyridines and/or prepolymers and polymers thereof;
   (F) allyl monomers and/or prepolymers thereof; or
   (G) mixtures of (A)–(F).

6. Copolymers of the reaction product of claim 1 with
   (A) styryl pyridines and/or prepolymers and polymers thereof;
   (B) vinyl styryl pyridines and/or prepolymers and polymers thereof;
   (C) bismaleimides and/or polymaleimides;
   (D) alkenylphenol capped styryl pyridines and/or prepolymers and polymers thereof;
   (E) hydroxystyryl pyridines and/or prepolymers and polymers thereof;
   (F) allyl monomers and/or prepolymers thereof; or
   (G) mixtures of (A)–(F).

7. A cured composite which comprises the product obtained by curing the product of claim 1 with heat resistant fibers.

8. A cured composite which comprises the product obtained by curing the product of claim 2 with heat resistant fibers.

9. A cured composite which comprises the product obtained by curing the product of claim 3 with heat resistant fibers.

10. A cured composite which comprises the product obtained by curing the product of claim 5 with heat resistant fibers.

* * * * *

UNITED STATES PATENT AND TRADEMARK OFFICE
CERTIFICATE OF CORRECTION

PATENT NO. : 4,540,745

DATED : September 10, 1985

INVENTOR(S) : Robert E. Hefner, Jr.

It is certified that error appears in the above-identified patent and that said Letters Patent is hereby corrected as shown below:

Col. 2, line 43 add --a-- after "or".

Col. 2, line 45 delete "a" before formula.

Col. 6, line 37 "naphthanate"; should read --naphthenate--.

Col. 15, line 17 remove "a" from formula.

Signed and Sealed this

Sixth Day of May 1986

[SEAL]

Attest:

DONALD J. QUIGG

Attesting Officer

Commissioner of Patents and Trademarks